(12) United States Patent
Scherson et al.

(10) Patent No.: US 8,088,113 B2
(45) Date of Patent: Jan. 3, 2012

(54) PORTABLE ELECTROCHEMICAL DEVICES FOR DUAL ACTION WOUND HEALING

(75) Inventors: Daniel A. Scherson, Beachwood, OH (US); Srinivasan Sarangapani, Walpole, MA (US); Lawrence J. Cali, East Falmouth, MA (US); Melvyn I. Burk, Beachwood, OH (US)

(73) Assignee: Neogenix, LLC, Fort Lauderdale, FL (US)

( * ) Notice: Subject to any disclaimer, the term of this patent is extended or adjusted under 35 U.S.C. 154(b) by 559 days.

(21) Appl. No.: 11/913,885

(22) PCT Filed: May 10, 2006

(86) PCT No.: PCT/US2006/018031
§ 371 (c)(1),
(2), (4) Date: Sep. 4, 2008

(87) PCT Pub. No.: WO2006/122169
PCT Pub. Date: Nov. 16, 2006

(65) Prior Publication Data
US 2009/0149821 A1 Jun. 11, 2009

(51) Int. Cl.
*A61F 13/00* (2006.01)

(52) U.S. Cl. .................................................. 604/305
(58) Field of Classification Search .......... 604/304–308, 604/290; 602/2; 607/50
See application file for complete search history.

(56) References Cited

U.S. PATENT DOCUMENTS 5,788,682 A * 8/1998 Maget .......................... 604/290
7,195,624 B2 * 3/2007 Lockwood et al. ........... 604/543

FOREIGN PATENT DOCUMENTS

WO WO 03049660 * 6/2003
* cited by examiner

*Primary Examiner* — Manuel Mendez
(74) *Attorney, Agent, or Firm* — Fay Sharpe LLP

(57) ABSTRACT

A portable, self-contained device is described for the topical application of oxygen and the removal of wound exudates to promote the healing of skin wounds. The device includes a wound dressing that incorporates at least one electrochemical cell for generating oxygen. The device can regulate the supply of oxygen to the wound at various concentrations, pressures and dosages and is used to produce a high concentration of oxygen at the wound site. By reversing the polarity of the power source a reduced pressure can be created in a reservoir attached to our device. The reduced pressure in the reservoir draws naturally flowing exudates away from the wound. Alternately, two reverse polarity cells are used to alternately supply oxygen and draw away exudates.

32 Claims, 3 Drawing Sheets

PORTABLE ELECTROCHEMICAL DEVICES FOR DUAL ACTION WOUND HEALING

BACKGROUND

The present exemplary embodiments relate to the expeditious removal of exudates from a wound site and the concurrent or subsequent delivery of pure oxygen to the Wound site to promote healing of venous stasis and diabetic foot ulcers and other wounds.

Accumulation of wound exudate increases patient discomfort and the potential for bacterial infection, and, thereby, affects adversely the healing process. In particular, chronic wound fluid blocks the proliferation and activity of fibroblasts and keratinocytes. In addition, it prevents easy reach of pure oxygen to the wound bed due to poor oxygen solubility in aqueous fluids, and, hence, the effectiveness of topical intermittent and transdermal sustained oxygen therapies. Chronic wounds are often heavily colonized with bacterial organisms and, therefore, timely removal of exudate is essential to minimize bio-burden. Wound cleansing removes contaminants from the wound surface and renders the wound less conducive to microbial growth. Wounds with foul smelling drainage are generally infected or filled with necrotic debris, and healing time is prolonged as tissue destruction progresses. The fluid of wound edema contains proteolytic enzymes, bacterial toxins, prostaglandins, and necrotic debris, all of which contribute to prolonged chronic inflammation.

Various types of wound dressings and drainage devices have been reported in the patent literature. Thus, a multipurpose wound dressing is described by Ewall, in U.S. Pat. No. 5,607,388. This patent teaches the use of a multiple layer wound dressing with sequentially removable layers that can be used to control the accumulation of exudate.

A general purpose surgical drain is described in U.S. Pat. No. 3,753,439. This device is a drainage conduit packed inside with soft, non-friable absorbent material. A suction line can be connected to the top of the fixture to drain the exudate.

Argenta and Morykwas (U.S. Pat. Nos. 5,636,643 and 5,645,081) patented a method of treating tissue damage by applying a negative pressure to a wound sufficient in time and magnitude to promote tissue migration and thus facilitate wound closure. Negative pressures in the range of 2-7 inches of Hg are applied over the wound and the surrounding areas. The area around most wounds becomes swollen with intercellular fluid, which is not removed due to insufficient blood circulation, and further compromises blood circulation as time progresses. Application of vacuum over the wound and surrounding area forces the intercellular fluid to flow towards the negative pressure region. Since the wound is open and perhaps sees the most negative pressure, all the intercellular fluid ends up accumulating in the wound. A tube properly placed in the wound and connected to the external vacuum source removes the liquid as it accumulates. Application of negative pressure over the wound site enhances both blood circulation and tissue migration.

The present embodiments herein described differ substantially from that of Argenta and Morykwas in at least two important respects: first, it simply allows better access of oxygen to the tissue bed by removing the naturally secreted wound exudates, and, second, it does not produce a negative pressure directly at a wound site, unlike the Argenta and Morykwas device. It therefore does not induce gross fluid flow from the wound area (from the surrounding tissue bed) or migration of epithelial and/or subcutaneous tissue toward the wound. Any reduced pressure at the wound site is generally less than that experienced in the Argenta and Morykwas device.

Sustained oxygen delivery has been suggested (see, e.g., U.S. Pat. No. 5,578,022) as an effective tool to accelerate the healing process even in the case of chronic wounds. In order to realize the benefits of delivered oxygen, it is important that the access to the tissue bed by oxygen be uninhibited. Exudate accumulation normally prevents such easy access of oxygen to the tissue bed. The present embodiments relate to electrochemical, light-weight devices, capable of both removing exudates from the wound bed, and also of delivering oxygen to the wound. These devices use no mechanical pumps or compressed gases and can be directly attached to the affected limb/area allowing the patient to be ambulatory.

BRIEF SUMMARY

In accordance with one aspect, there is provided one type of such dual action device including a single cell that can alternately remove exudates from the wound bed and deliver purified oxygen to the wound. A second type of device incorporates two such cells, in which one of the cells removes the exudates from the wound to expose the tissue bed, whereas the other delivers oxygen to the wound either intermittently or continuously.

In accordance with a second aspect, there is provided a device for supplying oxygen and removing exudates for treatment of a skin wound comprising a sealed housing; a conduit fluidly connecting the housing to the skin wound; and an electrochemical cell incorporated within the housing for alternately supplying oxygen to the skin wound and drawing exudates away from the skin wound, the cell including: a) a first electrode; b) a membrane for diffusing the negative ions and/or neutral species therethrough; and c) a second electrode communicating with the electrolyte; wherein in a first operating mode, the first electrode reduces oxygen in a feed gas to negative ions and/or neutral species and the second electrode oxidizes the negative ions and/or neutral species to produce a high concentration of oxygen for supply to the skin wound; and further wherein in a second operating mode, the operation of the electrodes is reversed, producing a reduced pressure in the housing resulting in removal of exudates from the wound.

In accordance with a third aspect, there is provided a device for supplying oxygen and removing exudates for treatment of a skin wound comprising: first and second sealed housings; first and second conduits fluidly connecting the first and second housings to the skin wound; an oxygen generating cell positioned in the first housing for supplying oxygen to the skin wound according to an electrochemical process; an oxygen consuming cell positioned in the second housing for drawing exudates away from the skin wound by generating a reduced pressure at the wound site; a valve positioned in the second conduit; a wound dressing patch adapted to form an occlusive seal over the skin wound; and a third conduit equipped with an absorbing media fluidly connecting the second housing and a wound bed of the wound.

In a fourth aspect, there is provided a method for treating skin wounds, comprising the steps of: placing an oxygen generating device having first and second associated electrochemical cells in fluid communication with a skin wound; and a) using the first cell to generate oxygen from the atmosphere and supplying the oxygen to the skin wound; and b) using the second cell to consume oxygen present in a vicinity of the wound, thereby generating a reduced pressure that acts to suction exudates from the site of the wound.

DETAILED DESCRIPTION

One present embodiment involves a device incorporating two single cells, one which removes by suction exudates from the wound site, and the other, which generates oxygen to be delivered to the wound site. As envisioned, in this dual cell device, two cells are mounted on individual single chambers connected via passages to a main chamber where the exudates are collected.

Each of the units, or cells, used in the present embodiments may operate based on similar principles as those described in our earlier patent, U.S. Pat. No. 5,578,022, (incorporated herein by reference in its entirety) which has been commercialized by Ogenix Corporation under the name EpiFLO, and approved by FDA for the treatment of certain types of wounds. More specifically, it uses oxygen reduction at a high area gas permeable cathode yielding water as a product, and water oxidation at a high area gas permeable anode to generate pure oxygen. Both electrodes are attached to opposite surfaces of a thin polymer electrolyte membrane (PEM), e.g., Nafion®, in much the same way as in PEM fuel cells. As the gas permeability of the assembly is very low, operation of the device enriches the oxygen content of the side facing the anode, and, at the same time, depletes the oxygen content of the side facing the cathode.

Figure 1:
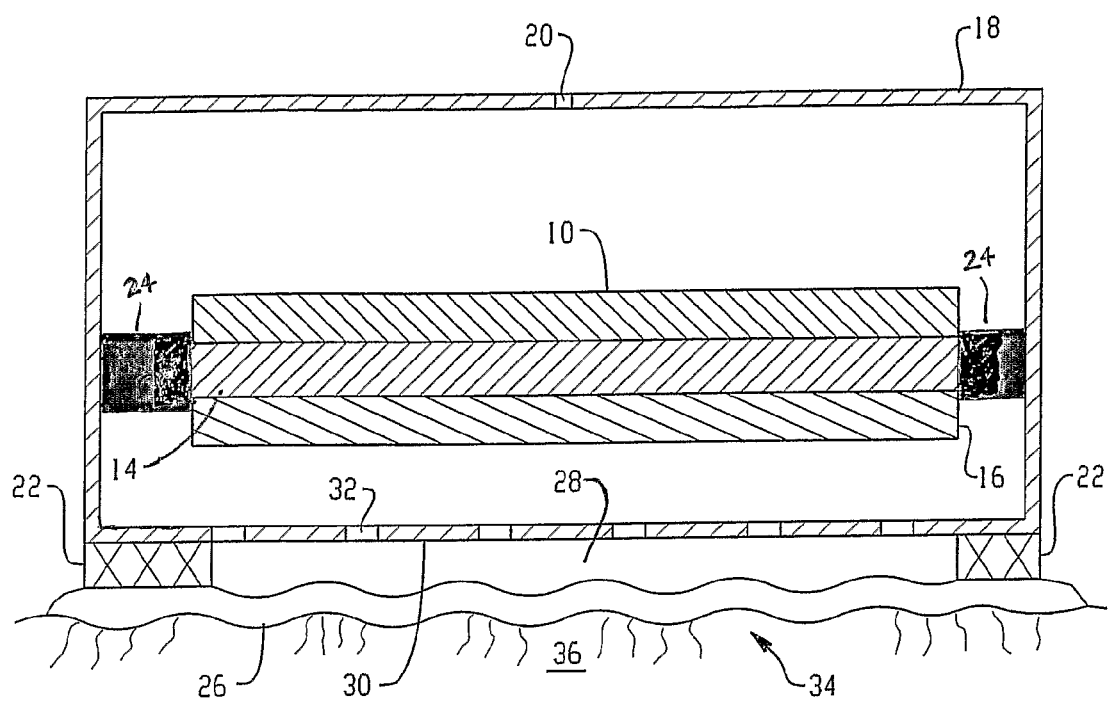
FIG. 1 is a schematic representation of a side view of an oxygen producing patch suitable for use with various embodiments of the invention.

With reference to FIG. 1, a side view of a basic oxygen producing device and patch assembly suitable for use with various aspects of the present embodiments is shown. The device includes a porous cathode 10, an ion conducting membrane 14 and a porous anode 16 inside a housing 18. The cathode is exposed to the atmosphere, such as through a vent 20, and the anode is exposed to or in communication with the skin wound 36. An impermeable barrier 24 separates the cathode and anode sides of the housing. Attached to a perimeter of an underside of the housing 18 is an adhesive strip 22, which completely encircles the base and is used to secure the device to the patient's skin 34 or a bandage 26 around the wound.

The adhesive strip 22 does not touch the wound, but serves to cause the housing of the device to stand off a slight distance from the wound itself, such that a cavity 28 is formed between a bottom of the housing 30 and the wound. This cavity 28 becomes filled with gaseous oxygen emitted from the interior of the housing through holes 32 on the bottom of the housing 30. Alternately, instead of holes 32, the bottom of the housing 30 may be formed of a material permeable to oxygen. The adhesive strip may be permeable to oxygen gas to prevent undue gas pressure from building up in the cavity 28. This permeability may be obtained by having formed valves or capillary holes through the adhesive layer (not shown) but preferably will be obtained by having the adhesive material itself be somewhat porous, since the formed passageways may have a greater tendency to allow contaminants to enter cavity 28 when the device is not operating. The oxygen pressure in the cavity 28 will vary depending on the permeability of the housing bottom, the number of valves and the identity of the adhesive material, and the rate of oxygen production. However, the pressure will preferably not exceed about 20-30 mm Hg to prevent vasoconstriction.

Adhesive is depicted at 22 for affixing the patch over a skin wound such that oxygen cannot flow readily out of the treatment area. As stated, the patch will generally have one or more one-way valves or small capillary holes to permit outflow of air. The patch may be incorporated into, include, or be deployed on top off or underneath one or more bandage layers 26. The bandage itself may have multiple layers to promote patient comfort and healing, including but not limited to layers of cotton gauze, polyethylene oxide-water polymer, as well as layer(s) containing topical ointments and other medicines including antibiotics, antiseptics, growth factors and living cells. Preferably, the bandage is occlusive on all sides and offers anti-microbial control without antibiotics or antiseptics, although these can still be used for added protection.

Positioned between the anode 16 and the cathode 10 is an ion conducting membrane 14. At electrode 10 a cathodic reaction occurs to combine the ambient oxygen from the air into water, in which it is present as reduced oxygen. The voltage differential created by electrodes 10 and 16 drives the species across the membrane 14, which is specific to passage of that species. At anode 16, an anodic reaction occurs to convert the species to release the reduced oxygen as gaseous oxygen onto the wound site.

With this unit, dioxygen supplied from the atmospheric air is reduced at the gas-permeable cathode 10 to negatively charged ions i.e. superoxide and peroxide and their various unprotonated and protonated states ($HO_2^0$, $HO_2^-$, $O_2^{2-}$) or hydroxyl ions or undissociated $H_2O_2$ according to a one, two or four electron process. The cathode may be of the type used in fuel cells. One or more of these species then travel through the thin separator/electrolyte structure or membrane 14 to the gas permeable anode 18, where they are reconverted into dioxygen. The dioxygen flows out of the anode and is intended to be directed to a skin wound.

The unit as shown in FIG. 1 may be powered by a variety of primary or secondary power sources, including alkaline manganese-dioxide, zinc-air, lithium thionyl chloride, lithium manganese dioxide, lithium ion, nickel metal hydride and the like.

Figure 2:
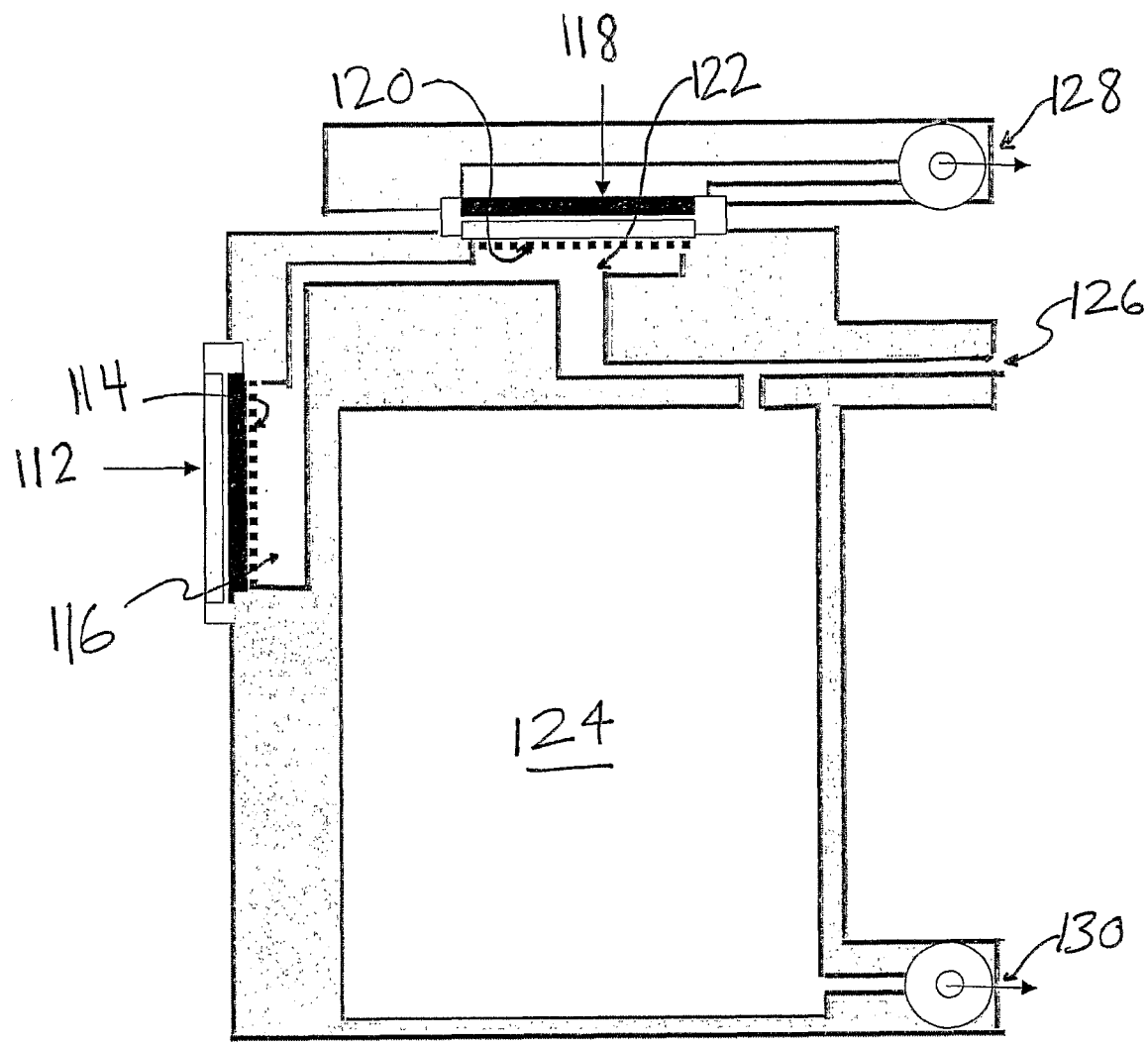
FIG. 2 is a schematic representation of a dual action oxygen delivery and wound exudates removal device according to one embodiment.

With reference now to FIG. 2, a device according to one embodiment of the present invention having a similar housing design as in FIG. 1, but utilizing two such electrochemical units or cells is shown. A first cell 112 has its anode 114 (oxygen generating electrode) exposed to an associated first chamber 116, while a second cell 118 has its cathode 120 (oxygen reducing electrode) exposed to its own adjoining chamber 122. Although the two devices are shown mounted on different side walls of the device, other configurations may also be envisioned, and as such are also covered by this invention. Regardless of their geometrical disposition, the entire device is so designed to prevent wound exudate from contacting the cells in almost any orientation, thus making the device wearable and portable. The second cell 118 or pump cell, when powered by a constant voltage, consumes oxygen from the main reservoir 124, thereby reducing the pressure therein, drawing by suction, exudates from the wound through an inlet 126 into its main reservoir 124. The consumed oxygen is evacuated to the atmosphere via an exhaust port 128. First or oxygen generating cell 112, when powered at constant current, continuously generates oxygen at rates of several ml/hr. The current flow in the pump cell 118 is preferably many times larger than the oxygen-generating cell 112.

The device can be designed so that the main reservoir 124 with the collected exudate can be easily detached from the cells and power/control electronics. In this respect, a drain port 130 in fluid contact with the main reservoir 124 can be incorporated into the device for easy draining of the collected exudates. Alternately, or in addition to this, the reservoir and/or other parts of the housing can be made disposable, such that a user would merely need to remove the cells from one housing and put them in a new housing, without the need to drain or remove the collected exudates.

This will allow a single device to provide exudate collection for extended periods. Also, a gas permeable membrane or membranes (not shown) impervious to liquids can be added between the cells and main reservoir 124 and/or inlet 126 to further ensure water or exudates from contacting the cell and its components. In a preferred mode of operation, the oxygen generating cell 112, is preferably constantly "ON" and provides a uniform oxygen flow to the wound, except for brief periods during which the suction mode of the first device is in operation, while the suction cell 118 preferably operates only for a short period of time, e.g., 2 minutes, and then switched off, in a cyclic fashion.

Figure 3:
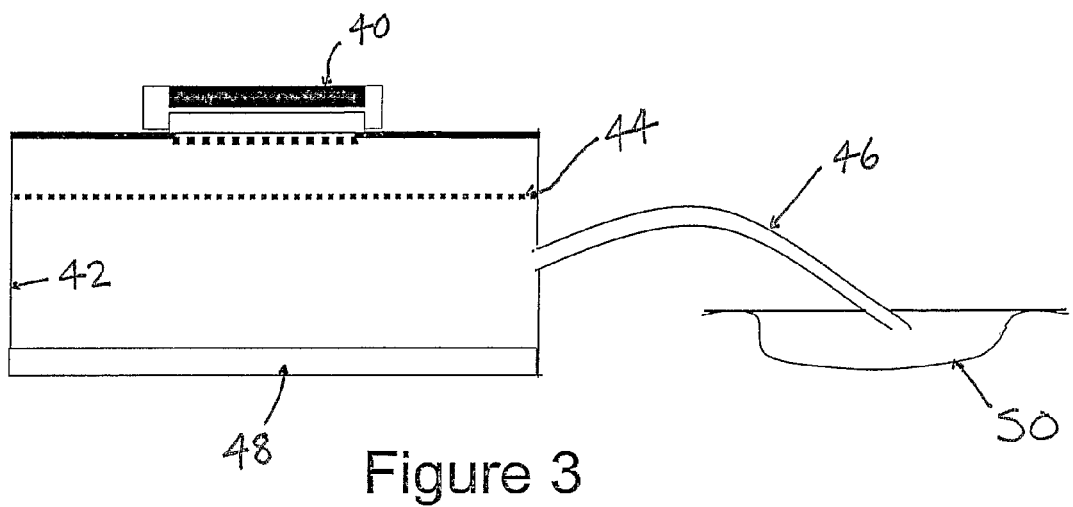
FIG. 3 is a schematic representation of a dual action oxygen delivery and wound exudates removal device according to another embodiment.
Figure 4:
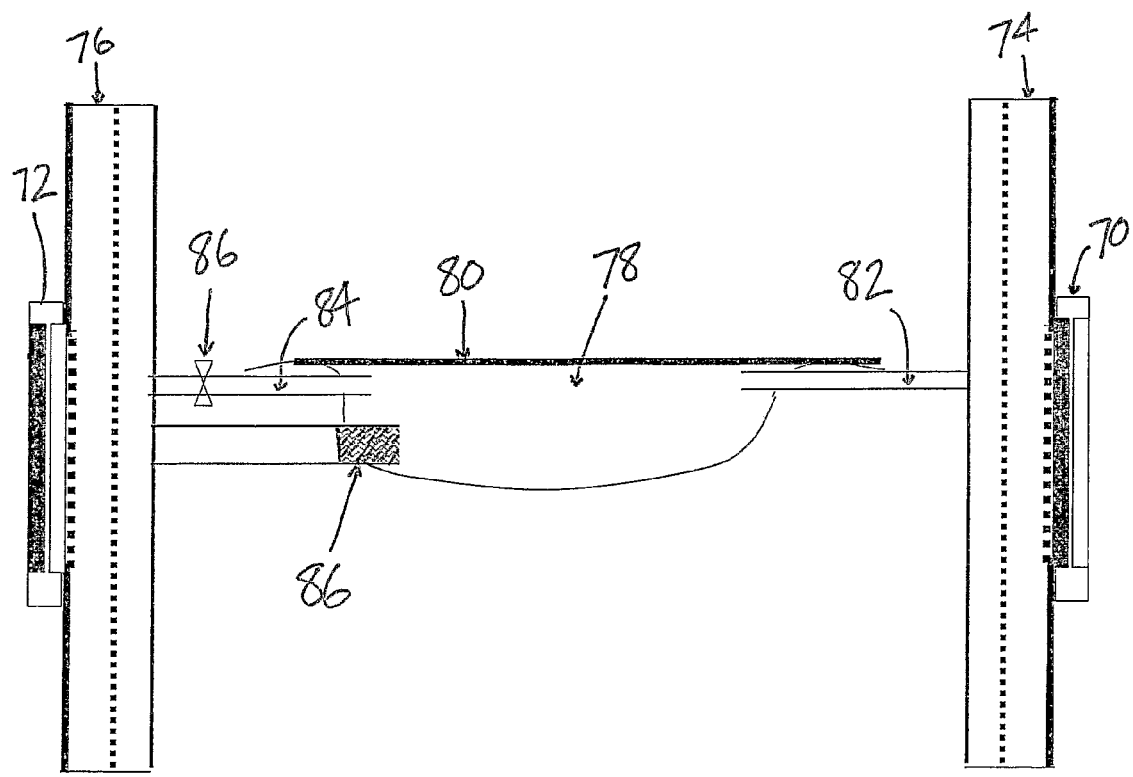
FIG. 4 is a schematic representation of a dual action oxygen delivery and wound exudates removal device according to still another embodiment.

In a second embodiment as shown in FIG. 3, there is provided a device incorporating a single cell that removes exudates from the wound site using suction created by the device itself, and then generates oxygen which is delivered to bare wound, in an alternating fashion. An electrochemical cell as detailed above with associated power supply 40 is mounted on one of the walls of a hermetically sealed box 42. In an exemplary device, the box may be of approximately 30 ml capacity. The cell is sealed to the wall of the box such that an electrode of the cell is in contact with the sealed interior of the box. A gas permeable barrier layer 44 (e.g., EPTFE, see dotted line in the figure above) is placed adjacent to the cell and separates the cell from the main interior volume of the box to prevent exudates from contaminating cell components. The box 42 is fitted with a cannula or conduit 46 such as a flexible tubing, which is sealed on one of the walls of the box below the barrier layer, in a leak-free manner and provides fluid communication between the interior of the box and the wound. The cannula may include a Luer type connection or similar type. The cannula is preferably made from a polymeric material suitable for use in hospital applications. Suitable materials for use in the cannula include, but are not limited to, silicone, polyethylene, polypropylene, polyurethane and various other thermoplastics.

The device will have either an integral or removable trap arrangement 48 for the exudates. In a preferred arrangement, the cell 40 is preferably mounted on the top or an upper wall of the box, while the exudates collects at the bottom of the box. Such an arrangement allows for the free-flow of gaseous oxygen between the wound and the cell, which will bypass the accumulated exudate in the box.

The power supply associated with the cell 40 is capable of operating in either a constant current or a constant voltage mode. In a typical operation cycle, the power supply is switched to a constant voltage mode, with the voltage pre-set at a prescribed level to limit the current to a 50-100 mA range, with the electrode facing the holes polarized at a potential negative enough to reduce oxygen in the box, and thereby decrease the pressure therein. This creates a suction through the cannula, which is placed in a wound bed 50. This draws exudates 52 accumulated in the wound bed into the box. This suction cycle is expected to last only 2-4 minutes. If there is no exudate left, then a partial vacuum of very low magnitude will be created, which will be equalized either by leak of air into the wound or by incoming oxygen during the oxygen generation cycle.

In the second stage, operation of the device is switched into a constant current mode with the polarity reversed such that the electrode facing the holes will generate oxygen, which will then be carried to the wound via the cannula tubing. The cycles can be repeated at pre-set periods of suction and oxygen generation using conventional electronic circuitry.

Depending on the type of wound and the dressing used to cover it, the tubing can contact the dressing in various ways. For example, the end of the cannula may be placed directly above the wound and under fully occlusive dressings, thereby making an ordinary bandage "oxygen enriched".

For in vivo uses, the end of the cannula can be implanted to the site where treatment is desired. The implanted end of the cannula may be perforated with multiple holes or made of material that would allow oxygen to diffuse through the tubing wall into ischemic tissue or the bloodstream. In addition, a syringe can be attached to the end of the tubing to facilitate the introduction of oxygen subdermally. Site specific oxygen delivery to promote localized angiogenesis or ischemic reperfusion and elevated metabolism is beneficial for orthopedic and organ repair as well as tissue, bone, tendon, and cartilage regeneration. Localized oxygenation of tissue and tumors for improved radiological oncology applications may benefit with the present device.

Thus, the present device may be considered a universal remote supply of oxygen in that it can be used with a wide variety of bandages or dressings already on the market. Additional types of dressings with which the present invention may be used include fully occlusive thin film dressings, hydrocolloid dressings, alginate dressings, antimicrobial dressings, biosynthetic dressings, collagen dressings, foam dressings, composite dressings, hydrogel dressings, warm up dressings, and transparent dressings.

In a third embodiment, there is provided a dual action device including two cells and a snorkel or valve arrangement. This example uses first and second cells 70 and 72 and incorporates in addition a snorkel or valve type arrangement to prevent interference of operation of the first cell from the second cell and vice versa. First and second cells 70 and 72 are housed in first and second sealed boxes 74 and 76. The wound site 78 is covered with a wound dressing patch that forms an occlusive seal 80 that at least substantially prevents air from the atmosphere from contacting the wound. Cannulas 82 and 84 connecting the boxes 74 and 76 with the wound are provided. Cells 70 and 72 are configured such that first cell 70 is configured to produce oxygen within the box 74, while second cell 72 is configured to consume oxygen from the box 76. If first cell 70 is turned on, oxygen will be produced within the box 74 and the partial pressure of oxygen will increase therein. Pressurization is avoided by allowing the gas to flow through the cannula 82, into the wound site 78 and through cannula 84 into cell 72. A check valve 86 positioned in cannula 84 is opened. The pressurized oxygen is allowed to escape through a small hole incorporating a snorkel type arrangement (not shown) in the seal 80.

Once cell 70 has been in operation for a while, thereby exposing the wound and cell 72 to a highly enriched oxygen atmosphere, it is then turned off, cell 72 is turned on, and the valve 86 is closed. Oxygen consumption at the cathode in cell 72 will decrease the total pressure within the compartment which, aided by the snorkel which closes the hole in the seal 80 upon a reduction in pressure, provides an occlusive seal over the wound. An absorbing media 86 immersed in the exudates is interposed between cell 72 and the wound, such that exudate is forced by the pressure differential out of the wound area and accumulates in the absorbent 86. Alternate use of this dual device arrangement will allow, as stated above, both bathing the wound with oxygen and removal of the exudate as required for wound healing. In one embodiment, the negative pressure at the wound is less than 2 inches of Hg.

Other similar arrangements can be thought of with one or two cells. In one example, an electrochemical cell is sealed in a two chamber (A and B) box, thus isolating the anode from the cathode compartments. The cathode compartment is equipped with a solenoid-actuated valve, which in turn is controlled by a control circuit. The control circuit energizes the solenoid on a pre-programmed duty cycle. The solenoid is normally open and energized to close.

A cannula from the anode chamber delivers pure oxygen to the wound. Another cannula is placed in the bottom of the wound either by itself or inserted into a capillary bed (e.g., a piece of absorbent material or hydrogel dressing). The distal end of this cannula in the wound exudate is then connected to an exudate waste container. The container houses an absorber that can take up the wound exudate. The exudate container also houses an outlet (with a goose neck arrangement) which is connected to the cathode chamber of the device through a one-way check valve. The exudate container is so designed as to make removal and disposal easy. When the device operates, the wound bed is delivered pure oxygen. During normal operation (or oxygen delivery cycle), the solenoid is open to atmosphere, allowing air access to the cathode of the cell.

During the exudate removal cycle, the solenoid is closed for a predetermined time, during which the oxygen in the cathode chamber is consumed, thus allowing a decrease in pressure. This causes the wound exudate to be drained into the exudate waste container. The solenoid valve is opened at a predetermined duty cycle to alternately allow air access and to create pressure differential between the cathode chamber and the wound. By this means, the wound is allowed access to pure oxygen, while removing excess exudate from the wound bed.

In another example, two cells are employed in series. The anode chamber of the first device is connected to the wound in substantially the same manner as described above. The anode outlet of a second oxygen-concentrating device is connected to the cathode chamber of the first device via a conduit or connecting tube. A check valve is placed in the connecting tube, with the flow direction allowing flow from the second device to the first. The second device is operated intermittently (at a pre-determined duty cycle) so as to periodically fill the cathode chamber of the first device with oxygen. The cathode chamber of the first device is also fitted with a check valve to allow purging of the cathode chamber initially and subsequently, when necessary. When the oxygen is consumed in the cathode chamber of the first device, due to the presence of pure oxygen, the pressure differential generated is substantially more than that in the previous example. Thus, when the polarity of the first device is reversed in order to draw exudates away from the wound, due to the higher pressure differential, the exudate suction is accomplished more efficiently. The exudate flow is contained in a disposable container in much the same way as described in the previous example.

What is claimed is:

1. A device for supplying oxygen and removing exudates for treatment of a skin wound comprising:
    a sealed housing adapted to cover said wound;
    an oxygen generating cell fluidly connected to said housing for supplying oxygen to the skin wound according to an electrochemical process; and
    an oxygen consuming cell fluidly connected to said housing for drawing naturally flowing exudates away from said skin wound by generating a reduced pressure in said housing;
    wherein said device is designed such that exudates from said wound are prevented from contacting said oxygen generating and oxygen consuming cells regardless of the orientation of said device.

2. A device according to claim 1, wherein said oxygen consuming cell draws exudates away from said skin wound by consuming oxygen present in said housing, thereby generating a reduced pressure therein that acts to suction exudates from the site of said wound.

3. A device according to claim 1, further comprising a reservoir for containing exudates withdrawn from said wound.

4. A device according to claim 3, wherein said oxygen generating cell, said oxygen consuming cell and said reservoir are all integral to said housing.

5. A device according to claim 3, wherein said reservoir is detachable from said housing.

6. A device according to claim 5, wherein said reservoir is disposable.

7. A device according to claim 1, wherein said device is capable of sustained transdermal oxygen delivery to said wound.

8. A device according to claim 1, wherein a supply of oxygen to said wound may be modulated between 0% and 100% oxygen concentration.

9. A device according to claim 1, wherein the oxygen generating and oxygen consuming cells generate and consume oxygen via an electrochemical reaction and include:
    a cathode for reducing oxygen in a feed gas to negative ions and/or neutral species;
    an electrolyte for diffusing the negative ions and/or neutral species therethrough; and
    an anode communicating with the electrolyte for oxidizing the negative ions and/or neutral species to produce oxygen.

10. A device according to claim 9, wherein the production of oxygen occurs according to a one, two or four electron process.

11. A device according to claim 9, wherein the negative ions are peroxide ions in their various unprotonated and protonated forms.

12. A device according to claim 9, wherein the negative ions are superoxide ions including their protonated form.

13. A device according to claim 9, wherein the negative ions are hydroxyl ions and the overall process involves electrolysis of water.

14. A device according to claim 1, wherein said device further includes a power source which applies a potential difference between a cathode and anode.

15. A device according to claim 14, wherein said power source is selected from the group consisting of capacitors, supercapacitors, photovoltaic cells, batteries, and alternating current power.

16. A device according to claim 14, wherein polarity on the power source is reversible to modulate a concentration of oxygen in the vicinity of said wound.

17. A device according to claim 1, wherein the oxygen generating cell is able to deliver oxygen to the skin wound at various pressures ranging from below atmospheric pressure to above atmospheric pressure.

18. A device according to claim 1, further comprising:
a gas permeable membrane for preventing the exudates from contacting the oxygen consuming cell.

19. A device for supplying oxygen and removing exudates for treatment of a skin wound comprising:
a sealed housing; a conduit fluidly connecting said housing to said skin wound; and
an electrochemical cell incorporated within the housing for alternately supplying oxygen to the skin wound and drawing exudates away from said skin
  a) a first electrode;
  b) a membrane for diffusing the negative ions and/or neutral species therethrough; and
  c) a second electrode communicating with the electrolyte; and
  d) a gas permeable barrier layer in said housing positioned between said cell and an inlet of said conduit;
  wherein in a first operating mode, said first electrode reduces oxygen in a feed gas to negative ions and/or neutral species and said second electrode oxidizes the negative ions and/or neutral species to produce a high concentration of oxygen for supply to the skin wound; and further wherein in a second operating mode, the operation of said electrodes is reversed, producing a reduced pressure in said housing resulting in removal of exudates from said wound.

20. A device according to claim 19, further comprising a power supply.

21. A device according to claim 20, wherein said power supply is able to operate in either a constant current or constant voltage mode.

22. A device according to claim 20, wherein said power supply comprises a bipolar battery.

23. A device according to claim 22, wherein said device can be switched between said first and said second modes of operation by reversing a polarity in said power supply.

24. A device according to claim 19, wherein said oxygen can be delivered to said wound subdermally and said removal of exudates is from a wound bed of said wound.

25. A device according to claim 19, further comprising a second electrochemical cell, wherein said second electrochemical cell is connected to the second electrode of said first electrochemical cell by a conduit having a valve that can be switched to allow or deny fluid connectivity between said first and second electrochemical cells.

26. A device according to claim 19, further comprising a reservoir for containing exudates withdrawn from said wound.

27. A device according to claim 26, wherein said reservoir is integral to said housing.

28. A device according to claim 26, wherein said reservoir is detachable from said housing.

29. A device according to claim 28, wherein said reservoir is disposable.

30. A device according to claim 26, further comprising:
a drain port in fluid contact with the reservoir for draining contained exudates.

31. A device for supplying oxygen and removing exudates for treatment of a skin wound comprising:
first and second sealed housings;
first and second conduits fluidly connecting said first and second housings to said skin wound;
an oxygen generating cell positioned in said first housing for supplying oxygen to the skin wound according to an electrochemical process;
an oxygen consuming cell positioned in said second housing for drawing exudates away from said skin wound by generating a reduced pressure in said second housing;
a valve positioned in said second conduit;
a wound dressing patch adapted to form an occlusive seal over said skin wound; and
a third conduit equipped with an absorbing media fluidly connecting said second housing and a wound bed of said wound.

32. A device according to claim 31, wherein said oxygen consuming cell and said oxygen generating cell comprise:
  a) a first electrode;
  b) an electrolyte for diffusing negative ions and/or neutral species therethrough; and
  c) a second electrode communicating with the electrolyte.

* * * * *